United States Patent [19]
Lartigue et al.

[11] 3,939,041
[45] Feb. 17, 1976

[54] METHOD OF MAKING FRUCTOSE

[75] Inventors: Donald J. Lartigue, Corning; Howard H. Weetall, Elmira, both of N.Y.

[73] Assignee: Corning Glass Works, Corning, N.Y.

[22] Filed: May 31, 1974

[21] Appl. No.: 475,157

[52] U.S. Cl. .................... 195/31 F; 195/65
[51] Int. Cl.$^2$ ............................ C12D 13/00
[58] Field of Search ............ 195/31 F, 65, 63, 68

[56] References Cited
UNITED STATES PATENTS

| | | | |
|---|---|---|---|
| 3,574,062 | 4/1971 | Sato ..................................... | 195/63 |
| 3,639,558 | 2/1972 | Csizmas ............................... | 195/68 |
| 3,706,633 | 12/1972 | Katchalski et al. .................. | 195/68 |
| 3,817,832 | 6/1974 | Llyod et al. ......................... | 195/31 F |
| 3,821,086 | 6/1974 | Lee et al. ............................. | 195/31 F |
| 3,843,442 | 10/1974 | Moskowitz .......................... | 195/31 F |

OTHER PUBLICATIONS

Weetall, "Immunoadsorbent for the Isolation of Bacterial Specific Antibodies," J. Bact. Vol. 93 No. 6, pp. 1876–1880 (1967).

*Primary Examiner*—A. Louis Monacell
*Assistant Examiner*—Thomas G. Wiseman
*Attorney, Agent, or Firm*—James A. Giblin; Clinton S. Janes, Jr.; Clarence R. Patty, Jr.

[57] ABSTRACT

Bacterial cells (*Streptomyces sp.*) having glucose isomerase activity can be aggregated with an aqueous solution of tetrazotized benzidine and used as an immobilized enzyme system for the isomerization of dextrose (glucose) to levulose (fructose).

1 Claim, No Drawings

METHOD OF MAKING FRUCTOSE

BACKGROUND OF THE INVENTION

Various immobilized glucose isomerase systems have been developed for the enzymatic conversion of glucose to fructose. See, for example, U.S. Pat. No. 3,779,869 issued on Dec. 18, 1973. In many cases, the systems are relatively expensive and/or require fairly critical immobilization techniques or carrier materials. We have found a relatively simple and economical system useful for the preparation of fructose.

SUMMARY OF THE INVENTION

Our method of preparing fructose comprises the step of reacting an aqueous dextrose solution under incubating conditions with aggregated bacterial cells of an organism of the genus Streptomyces, the individual and aggregated cells demonstrating glucose isomerase activity, and the aggregated cells being the reaction product of a suspension of the individual cells and an aqueous solution of tetrazotized benzidine. The aggregated cells constitute an immobilized glucose isomerase system which can be readily separated from the reaction solution and reused.

SPECIFIC EMBODIMENTS

We have surprisingly found that the individual bacterial cells can be readily aggregated to form relatively water-insoluble clusters without significant loss in glucose isomerase activity by crosslinking the cells with a solution of tetrazotized benzidine having dissolved therein a preferred quantity of between about 4.0 to about 20.0 mg of tetrazotized benzidine per gram of cells to be aggregated. The crosslinked cells demonstrate maximum theoretical isomerization of dextrose to fructose and they can be readily removed from the reaction medium (e.g., by centrifugation) and reused.

PREPARATION OF THE AGGREGATES

Bacterial cells (*Streptomyces sp.*) obtained from Nagase & Co., Ltd., Tokyo, Japan, and having glucose isomerase activity, were crosslinked (aggregated) using varying amounts of tetrazotized benzidine (in solution) per gram of cells to note the effect of the amount of the crosslinking agents on the glucose isomerase activity of the aggregates. The crosslinking technique using the tetrazotized benzidine was similar to that described for the polymerization of spores of *Bacillus subtilis* var. *niger* and *Serratia marcescens*, but without any prior treatment of the cells, as shown in an article by H. Weetall entitled "Immunoadsorbent for the Isolation of Bacterial Specific Antibodies," J. Bact. 93, 1876–80 (1967).

Separate 250 mg samples of the dried Streptomyces sp. cells were each suspended in 10 ml. of 0.5 M NaHCO₃ solutions. The 10 ml. suspensions were then reacted separately with varying amounts of an aqueous tetrazotized benzidine solution (1 percent by weight or 10 mg per ml.) ranging from 0 to approximately 1 ml. at 0°C. The reactions were continued for two hours and the aggregated cells were centrifuged out (5000 rpm for 60 minutes), washed with distilled water, and assayed with a 2 M dextrose solution. The assay results are shown in Table I where the concentration of tetrazotized benzidine (shown as mg of crosslinking agent per gram of cells) is shown opposite the glucose isomerase activity per gram of the aggregates formed with the indicated amounts of crosslinking agent. One unit of glucose isomerase activity represents the production of one $\mu$ mole of fructose per minute at pH 6.80 and 60°C.

TABLE I

| Activity (units/g cells) | Concentration (mg tetrazotized benzidine/g cells) |
| --- | --- |
| 145 | 0 |
| 170 | 0 |
| 150 | 4.0 |
| 125 | 8.0 |
| 135 | 16.0 |
| 100 | 17.5 |
| 120 | 19.0 |
| 85 | 31.0 |
| 85 | 35.0 |
| 73 | 40.0 |

EXAMPLE

A 6.5 gram batch of the crosslinked cells was prepared by suspending that quantity of the dried cells in 100 ml. of 0.5 M NaHCO₃ solution and reacting the suspension with 7.8 ml. of an aqueous solution of 1 percent by weight tetrazotized benzidine (78 mg). The reaction was continued for 60 minutes at 0°C. The aggregated cells were centrifuged out, washed, and assayed as above. The glucose isomerase activity of the large batch was found to be 70 units/gram of aggregate. The 6.5 gram batch was then placed in a one liter aqueous solution of 50 percent (weight) dextrose at 60°C. and stirred. Every 24 hours the substrate (dextrose solution) was changed and the percent isomerization of dextrose to fructose was determined, 50 percent conversion being the maximum percent theoretically possible. The results are shown in Table II.

TABLE II

| Time (days) | Fructose (%) | Accumulated Fructose (g) |
| --- | --- | --- |
| 0 | 0 | 0 |
| 1 | 50 | 250 |
| 2 | 50 | 500 |
| 3 | 50 | 700 |
| 4 | 50 | 1000 |
| 5 | 50 | 1250 |
| 6 | 1 | 1253 |
| 7 | 0 | 1253 |

The data of Table II indicate useful enzymatic life of about 5 days for the composite of the example.

We claim:

1. A method of preparing fructose from an aqueous dextrose solution which comprises the step of reacting the solution under incubation conditions with crosslinked bacterial cells of an organism of the genus Streptomyces, the crosslinked cells having glucose isomerase activity and being the reaction product of a suspension of individual cells having glucose isomerase activity and an aqueous solution of tetrazotized benzidine, the tetrazotized benzidine solution having dissolved therein between about 4.0 and 20.0 mg of tetrazotized benzidine per gram of cells.

* * * * *